Figure 1:
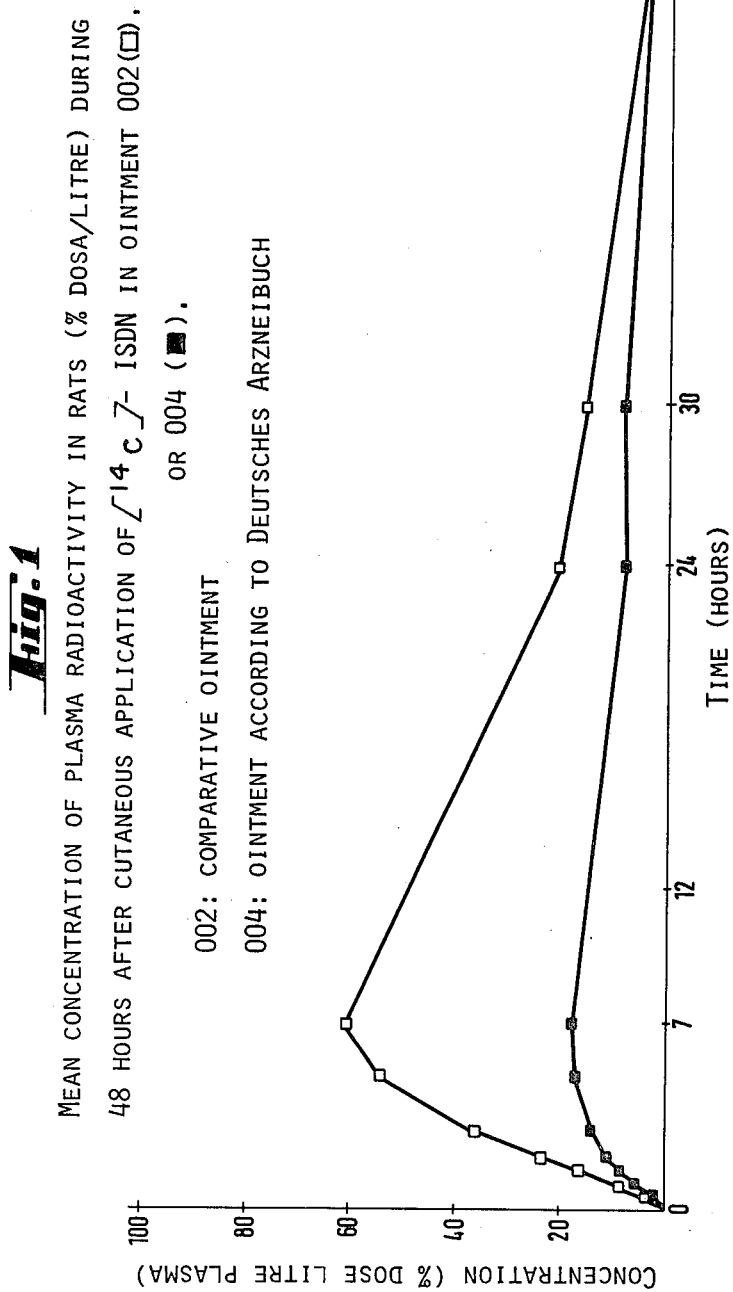

United States Patent [19]

Cordes et al.

[11] 4,293,565

[45] Oct. 6, 1981

[54] TRANSDERMAL MEDICATION SYSTEM FOR ISOSORBIDE DINITRATE

[75] Inventors: Günter Cordes, Leichlingen; Ewald Giesselmann; Ulrich Münch, both of Monheim, all of Fed. Rep. of Germany

[73] Assignee: Sanol Schwarz-Monheim GmbH, Monheim, Fed. Rep. of Germany

[21] Appl. No.: 82,490

[22] Filed: Oct. 9, 1979

[30] Foreign Application Priority Data

Jun. 13, 1979 [DE] Fed. Rep. of Germany ....... 2924005

[51] Int. Cl.$^3$ ............................................ A61K 31/34
[52] U.S. Cl. ................................................. 424/285
[58] Field of Search ......................................... 424/285

[56] References Cited

U.S. PATENT DOCUMENTS 4,112,115 9/1978 Coghlan .............................. 424/300

OTHER PUBLICATIONS

U.S. Pharmacopeia XVIII, 1970, pp. 457, 809.

*Primary Examiner*—Frank Cacciapaglia, Jr.

[57] ABSTRACT

A pharmaceutical preparation comprising:
(a) isosorbide dinitrate as active ingredient
(b) a solvent for isosorbide dinitrate
(c) an ointment consistency agent
(d) an emulsifying agent
(e) water, and
(f) possibly customary preservatives, antioxidants, buffers and/or odorants;

where the weight ratio of water: consistency agent including emulsifying agent: solvent is 30 to 80: 3 to 35: 3 to 35, the amount of emulsifying agent is from 0% to 15% by weight and the amount of isosorbide dinitrate is from 2% to 20% by weight. The preparation has an ointment-like consistency and is administered topically to the skin, where it has a high adsorption rate and a long duration of response.

10 Claims, 3 Drawing Figures

TRANSDERMAL MEDICATION SYSTEM FOR ISOSORBIDE DINITRATE

The invention concerns a transdermal medication system for isosorbide dinitrate which can also be designated a pharmaceutical preparation containing isosorbide dinitrate.

Contrary to usual ointments the preparation according to the invention has a comparatively low viscosity so that it can be dosed without any problems. It has a high absorption rate (bioavailability) and a long duration of response. When applied to the skin, it is acceptable to the patient because it does not have a fatty character. Organic nitrates like nitroglycerin or isosorbide dinitrate are successfully used for the treatment of coronary heart diseases. During the last years results with nitroglycerin ointments have been reported which stress a longer efficiency compared with an oral application. Details can be drawn from the following Table 1.

TABLE 1

| Quotation | Effect (h) |
| --- | --- |
| (1) Meister et al., British Heart Journal, 38 (1976) 1031 etc. | 2 to 5 |
| (2) Parker et al., The American Journal of Cardiology, 38 (1976) 2: 162 etc. | at least 1 |
| (3) Reichek, Circulation, 50 (1974) 348 etc. | at least 3 |
| (4) Taylor, The American Journal of Cardiology, 38 (1976) 469 etc. | 3 to 6 |
| (5) Abrams, Clinical Research, 24 (1976) 79 A | at least 3 |
| (6) Hanak et al., Therapiewoche, 28 (1978) 40:7447/61 | 3 |
| (7) Armstrong, The American Journal of Cardiology, 38 (1976) 474 etc. | 3 to 4 |

U.S. Pat. No. 4,112,115 suggests the application of isosorbide dinitrate with a carrier, the isosorbide dinitrate being in true solution in one or several phases of the carrier. However, with such true solutions long time effects cannot be achieved.

A topical application of the organic nitrates mentioned offers the benefit over oral application because the active ingredients do not first enter the liver and then the systemic circulation.

In case of an oral application the active ingredients enter the liver immediately so that a remarkable portion of the active ingredient is metabolised to metabolites which are less active or inactive.

The invention starts from the problem to provide a pharmaceutical preparation which meets inter alia the following conditions for an application on human skin:

1. The preparation can be dosed quite exactly with an apparatus, for example, according to the German Pat. No. 16 25 200;
2. The applied preparation can be easily rubbed in and does not leave a repellant fatty or fat-like film or crust on the skin;
3. The preparation is characterized by a high resorption rate of the active ingredient without any use of known entraining substances like dimethyl sulfoxide or dimethyl acetamide; and
4. The preparation offers a long time effect because of a depot of undissolved active ingredient.

Figure 2:
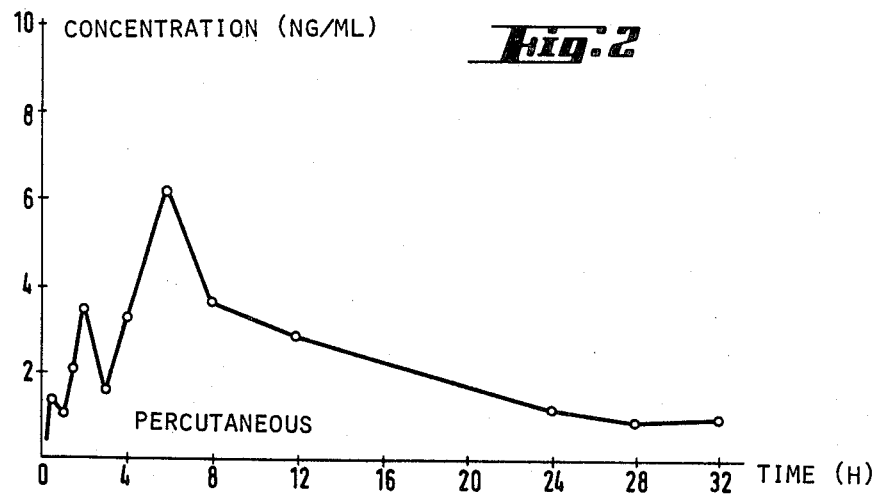
Figure 3:
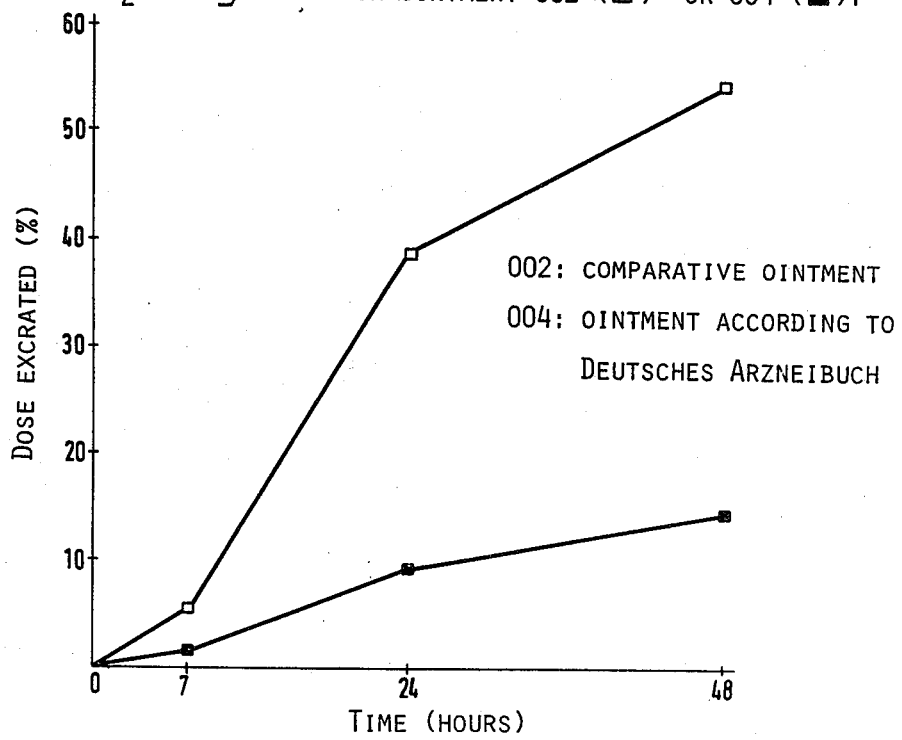

In the drawings,

FIGS. 1 and 3 are comparative graphs of the preparation of the invention and the prior art preparation and FIG. 2 is a graph of the amount of isosorbide dinitrate found in the blood plasma as a function of time when the preparation of the invention was applied percutaneously.

From FIG. 1 follows that only an unsatisfactory resorption rate for isosorbide dinitrate can be achieved when an ointment base according to Deutsches Arzneibuch is used.

PREPARATION

The problem from which the invention starts can be solved by a pharmaceutical preparation which consists of or contains (a) isosorbide dinitrate as active ingredient,
(b) a solvent for isosorbide dinitrate,
(c) an ointment consistency agent,
(d) an emulsifying agent,
(e) water and
(f) optionally usual preservatives, antioxidants pH regulators and/or fragrances where the proportion by weight of water: consistency agent including the emulsifying agent (d): solvent is 30 to 80: 3 to 35: 3 to 35, the amount of emulsifying agent (d) is 0.5 to 15% by weight (based on the preparation) and the isosorbide dinitrate amount is 2 to 20% by weight (based on the preparation).

The preparation according to the invention contains a solvent which dissolves at least 5 and especially at least 10% by weight isosorbide dinitrate (based on the solvent) and which is miscible and especially infinitely miscible with water and has an ointment-like consistency (solidifying point below 40° C.) or is liquid (boiling point more than 100° C.). Solvents having a lower volatility than water are preferred. Examples for such solvents are esters of a $C_{8-18}$ fatty acid with glycerin alkoxylated and especially ethoxylated with for example 3 to 10 mols and especially about 7 mols alkylene oxide.

The consistency agent can be a mono- or poly-ester of a polyfunctional aliphatic alcohol with a fatty acid having 8 or more carbon atoms or with a hydroxy fatty acid having 8 or more carbon atoms; or mono- or polyester of a polyfunctional aliphatic carbon acid with a fatty alcohol having 8 or more carbon atoms; a fatty alcohol having 10 or more carbon atoms and/or a fatty acid having 10 or more carbon atoms. Special examples for such consistency agents are glycerin monostearate, hardened castor oil, cetyl alcohol, stearyl alcohol and/or stearic acid.

The consistency agent can, in addition, have an emulsifying effect. It is possible to add an (additional) emulsifying agent (d) to the preparation according to the invention; the additional emulsifying agent can be an ester of a polyalkylene diol with a fatty acid or a polyalkylene diol which has been etherified with a fatty alcohol. The stearate of polyethylene glycol is an example (average molecular weight of polyethyleneglycol about 100). The concentration of the emulsifying agent (d) can be, for example, 1 to 10% by weight (based on the preparation).

The preparation according to the invention is characterized by a high water content. After an application to human skin, the temperature of which is about 30° C., the water content decreases and approaches an equilibrium. A solvent proportion of the preparation according to the invention can be selected in such a manner that the weight ratio of dissolved to undissolved isosorbide dinitrate is 1 to 60:99 to 40 and especially 5 to 60:95 to 40 when the equilibrium has been reached or approximately reached. These ranges guarantee that first the concentration of dissolved isosorbide dinitrate in the preparation is high enough in order to achieve a satisfactory resorption rate and that second the amount of undissolved isosorbide dinitrate in the preparation is great enough in order to achieve a long time effect. In vitro test with an ointment according to the invention were performed to determine the amount of dissolved and undissolved isosorbide dinitrate (ISDN) in the preparation after reaching the equilibrium. In each test, a film of 0.5 mm thickness was applied on an impermeable support at 30° C. at a humidity of the air of about 70%. After reaching an equilibrium a weight ratio of dissolved to undissolved isosorbide dinitrate of 1 to 60:99 to 40 and especially 5 to 60:95 to 40 was found.

At least 90% and especially 90% by weight of the isosorbide dinitrate particles contained in the preparation can have a length of less than 100 and especially less than 60 $\mu$m and a breadth of less than 20 and especially less than 10 $\mu$m. In this way a fast supplementary dissolution of isosorbide dinitrate crystals is possible.

PROCESS FOR THE PRODUCTION

The preparation according to the invention can be produced by (a) melting a mixture of isosorbide dinitrate, consistency agent, solvent and a facultative emulsifying agent (d) and (b) by chilling this melt in water. It is possible to start with selected total amounts or with partial amounts of the said components and to add the remaining amounts after the chilling step. The usual additives like preservatives, antioxidants, pH regulators and/or fragrances can be added to one or several of the said components before the production of the melt or can be added to the melt before the chilling step and/or after the said step. The process according to the invention guarantees that finely divided isosorbide dinitrate is formed, which enables a fast supplementary dissolution in the preparation.

In one embodiment of the invention the melt is formed at a temperature of about 55 to 77 and especially about 63 to 67° C. and added to water under stirring, the water having a temperature of about 0 to 25 and especially 1 to 5 and preferably 1° to 2° C.

An intensive stirring is preferred.

UNEXPECTED ADVANTAGES

The preparation according to the invention contains a large amount of water. Accordingly, the preparation can be dosed with a satisfactory exactitude with for example a dosimeter and can be easily rubbed into human skin without any remaining repellant fatty film. Clothes are not soiled so that the patient's attitude is not negatively influenced and no reason for an irregular application exists.

From the description of the process for the production according to the invention follows that a part of the dissolved isosorbide dinitrate is precipitated when the mixture of isosorbide dinitrate, solvent and consistency agent is added to water, i.e. the preparation according to the invention contains undissolved isosorbide dinitrate. The initial resorption is due to the dissolved active ingredient and the undissolved active ingredient acts as a depot and guarantees a long time effect.

The special process according to the invention offers the benefit of a fast supplementary dissolution since the chilling of the melt in water results in a finally divided active ingredient. Since, in addition, the concentration of dissolved active ingredient in the preparation is small, any recrystallization and any crystal growth are suppressed in a beneficial manner so that a fast supplementary dissolubility is maintained after the ointment was applied to the skin and the water equilibrium was reached. It is surprising that a good emulsion stability and a high resorption rate can be achieved. Especially with respect to the resorption rate experts would have expected an unsatisfactory result because of the high water content of the preparation according to the invention. (The saturation concentration of isosorbide dinitrate in water is merely about 0.7 g isosorbide dinitrate/liter of water.)

Because of the high water content, experts would have expected a small concentration of dissolved active ingredient and therefore a low resorption in addition and corresponding to the problem of the invention experts must not use usual entraining substances (like dimethyl sulfoxide or dimethyl acetamide, which are toxicologically critical).

Therefore, the long time effect in combination with a high resorption rate, which can be achieved according to the invention, are surprising (examples 2 to 3). Experts would not have achieved a correspondingly satisfactory result by omitting water. For example, a preparation of merely isosorbide dinitrate and an ointment base (without any water and isosorbide dinitrate solvent) would be fatty and not satisfactorily dosable and would give a low resorption rate. The resorption rate could be improved by adding a solvent, but a long time effect could not be achieved and the fatty character and not satisfactory dosability would be maintained. A long time effect also cannot be expected from the isosorbide dinitrate solution of the U.S. Pat. No. 4,112,115.

The following examples explain the invention, but are not limitative.

COMPARATIVE EXAMPLE 1 (FIGS. 1 and 3)

For the preparation of an ointment with 10% by weight isosorbide dinitrate a water containing hydrophilic ointment according to Deutsches Arzneibuch, 8th edition, page 436, was used; the isosorbide dinitrate was marked by radioactivity ($^{14}C$). At least 90% of the isosorbide dinitrate particles had a length of not more than 100 $\mu$m. This ointment was applied to rats (n=5); then the average radioactivity concentration in the plasma and the cumulative secretion into the urine were measured. The results can be drawn from FIGS. 1 and 3, 004. Dosability and resorption rate were unsatisfactory.

In addition, comparative ointment with the following composition was produced:

|  | % by weight |
|---|---|
| Isosorbide dinitrate | 10 |
| Solvent | 78 |
| ($C_{8-18}$ fatty acid ester of a glycerin ethoxylated with about 7 mols ethylene oxide) | |
| Consistency agent | 4 |
| (hardened castor oil) | |
| Emulsifying agent | 8 |

| | % by weight |
|---|---|
| (2-octyldodecanol) | |

Weight ratio consistency agent (including emulsifying agent): solvent =3:21.5.

This comparative ointment corresponded to an ointment according to the invention with the exception that the ointment did not contain any water when applied. Both this comparative ointment and the ointment according to Deutsches Arzneibuch had the same isosorbide dinitrate content of 10% by weight when applied.

The comparative ointment was applied to rats and tested in the same manner as the ointment according to Deutsches Arzneibuch.

In the case of the comparative ointment, the average radioactivity concentration in the plasma and the cumulative secretion into the urine were examined as in the case of the ointment according to Deutsches Arzneibuch. A faster resorption and therefore a higher plasma level and a higher resorption rate were achieved compared to the ointment according to Deutsches Arzneibuch.

By preceding tests it was possible to conclude that in case of an ointment according to the invention most of its water is evaporated after an application onto the skin. Therefore, after an application onto the skin and an establishment of a water equilibrium the composition of an ointment according to the invention with the following starting composition:

| | Parts by weight | % by weight |
|---|---|---|
| Isosorbide dinitrate | 10 | 5.0 |
| Solvent | 78 | 43.3 |
| Consistency agent | 4 | 2.2 |
| Emulsifying agent | 8 | 4.5 |
| Water | 80 | 44.5 |
| | | 100.0 |

Weight ratio water: consistency agent
(including emulsifying agent):
solvent=44.5:6.7:43.3
(=30:4.5:29.2)
corresponds practically to the composition of the before mentioned comparative ointment.

The long time effect of an ointment according to the invention of the following example 1 further improved since even after an application onto the skin and after an evaporation of water such an ointment contains undissolved isosorbide dinitrate which is dissolved gradually (depot effect of undissolved isosorbide dinitrate).

EXAMPLE 1

A preparation was produced according to the following formulation:

| | | |
|---|---|---|
| 1. | Isosorbide dinitrate | 20 kg |
| | Glycerin monostearate | 11 kg |
| | Polyoxy ethylene stearate (average molecular weight of polyoxy ethylene 100) | 9 kg |
| 2. | $C_{8-18}$ fatty acid ester of a glycerin ethoxylated with about 7 mols ethylene oxide | 20.0 kg |
| 3. | Sorbic acid | 0.33 kg |
| 4. | Ascorbylpalmitate | 0.11 kg |
| 5. | Citric acid | 0.2 kg |
| 6. | Sodium ethylene diamine tetraacetic acid | 0.028 kg |
| 7. | Creme perfume oil 0/017681 "Dragoco" | 0.1 kg |
| 8. | Water | 139.232 kg |
| | | 200.0 kg |

Starting materials 3 and 4 were carefully mixed with each other and ground with about 0.8 kg of starting material 2, which was added in small portions so that no lumps were formed.

From the starting materials 1 and the remaining 19.2 kg of the starting material 2 a clear melt was formed by heating to 70° to 75° C. in a reactor, which was equipped with a cover (which could be screwed down), an observation window and a stirrer. The melt was steadily stirred. Then a melt temperature of 63° to 67° C. was adjusted. To this melt the ground mixture of the starting materials 3 and 4 in the starting material 2 was added; the melt was stirred until a clear solution resulted. A cooling of the melt below 60° C. was avoided since then a precipitation of isosorbide dinitrate would have resulted which would have required a new heating step above 70° C. Such a new heating step, however, would have been a drawback for the stability of the ascorbylpalmitate.

The starting materials 5 and 6 were dissolved in a second reactor (Brogli) in water. This reactor was equipped with a stirrer and a homogenizer. The aqueous phase was cooled to 1° to 2° C. whereupon a vacuum of at least $-0.8$ kg/cm$^2$ was applied to the reactor. Then the melt was sucked into the reactor while the temperature of the melt was maintained at 63° to 67° C. and the homogenizer was still switched on. This sucking step took about 15 minutes. The system was further cooled during the sucking step.

After the sucking step had been finished the stirring was continued for one hour at a vacuum of less than $-0.8$ kg/cm$^2$. Then the starting material 7 was sucked into the reactor through the homogenizer while the system was stirred for an additional five minutes. Then the stirrer and homogenizer were switched off and the vacuum was broken by slow ventilation.

Several glass bottles were filled with 90 g of the preparation each. The glass bottles were equipped with cream pumps (LL 10 V, Deutsche Aerosol Ventile GmbH), the stroke of which was adjusted to 500 mg.

EXAMPLE 2

After a (nominal dosage) of 100 mg isosorbide dinitrate (based on the preparation according to Example 1) had been applied to human skin the average concentrations of the active ingredient were 1 to 2 ng/ml (nanogram/milliliter—a nanogram is 1 gram×10$^{-9}$) during the first one and a half hours and reached 6.2 ng/ml after 6 hours. Then the values dropped gradually to 2.9 ng/ml after 12 hours and to 1.2 ng/ml after 24 hours. A measurable level of the active ingredient existed even after 32 hours.

In the case of a sublingual application of a tablet with 5 mg isosorbide dinitrate the highest level of the active ingredient in the plasma (15.9 ng/ml) was reached after 0.5 hours; then the level dropped with a half-life period of about 50 minutes.

This means that after a cutaneous application of isosorbide dinitrate levels of the active ingredient result in the plasma which are maintained for a relatively long period. For further details compare Mansel-Jones et al. in Therapiewoche, 28 (1978) 6537 to 6540.

EXAMPLE 3

Eleven patients with a clinically and electrocardiographically confirmed coronary heart disease were treated with a preparation according to Example 1. At the beginnning of the treatment and after 3, 5 and 7 hours the ST line decrease was measured (under ergometric control), which reflects the coronary heart disease and the efficiency of the drug respectively. ST line decrease of 2.7 mm (reference value) was measured at the beginning of the treatment. The ST line decrease was 1.2 mm three hours after the application of the preparation, 1.0 mm five hours after the application and 0.9 mm seven hours after the application; a drop in the efficiency could not be observed even after 7 hours. This means that the efficiency is maintained for more than seven hours. (Publication by Professor Brunner, Donolo Hospital, Jaffa/Israel; in print).

We claim:

1. A pharmaceutical preparation consisting essentially of
   (a) isosorbide dinitrate as active ingredient,
   (b) a non-aqueous solvent for isosorbide dinitrate which dissolves at least 5% by weight of isosorbide dinitrate, based on the solvent, has an ointment-like consistency and is miscible with water, where said solvent is an ester of a $C_{8-18}$ fatty acid with glycerin ethoxylated with from 3 to 10 mols of ethylene oxide,
   (c) an ointment consistency agent selected from the group consisting of glycerin monostearate, hardened castor oil, cetyl alcohol, stearyl alcohol, stearic acid, and mixtures thereof, and
   (d) water,
where the weight ratio of water to consistency agent to solvent is 30 to 80:3 to 35:3 to 35 and the amount of isosorbide dinitrate in the preparation is from 2% to 20% by weight.

2. The pharmaceutical preparation of claim 1, having a further content of (e) from 0.5% to 15% by weight based on the preparation of an emulsifying agent, said emulsifying agent being considered as part of said consistency agent with respect to said weight ratio, and being selected from the group consisting of esters of a polyoxyalkylene diol with a fatty acid and polyoxyalkylene diols etherified with a fatty alcohol.

3. The pharmaceutical preparation of claim 1 wherein said fatty acid ester of glycerin is ethoxylated with about 7 mols of ethylene oxide.

4. The pharmaceutical preparation of claim 2 wherein said ester of a polyoxyalkylene diol with a fatty acid is the stearate of a polyoxyethylene glycol having an average molecular weight of said polyoxyethylene glycol of about 100.

5. The pharmaceutical preparation of claim 2 wherein component (e) is present in an amount of from 1% to 10% by weight.

6. The pharmaceutical preparation of claim 1 or 2, wherein said non-aqueous solvent dissolves at least 10% by weight of isosorbide dinitrate, based on the solvent, and is infinitely miscible with water.

7. The pharmaceutical preparation of claim 1 or 2 wherein the amount of said non-aqueous solvent is so selected that the ratio by weight of dissolved to undissolved isosorbide dinitrate is from 1 to 60:99 to 40, after application of the preparation to the human skin and after reaching of a water equilibrium.

8. The pharmaceutical preparation of claim 7 wherein said ratio by weight is from 5 to 60:95 to 40.

9. The pharmaceutical preparation of claim 1 or 3 wherein at least 90% by weight of the isosorbide dinitrate is present as particles having a length of at most 100 $\mu$m and a breadth of at most 20 $\mu$m.

10. The pharmaceutical preparation of claim 9 wherein said isosorbide dinitrate particles have a length of less than 60 $\mu$m and a breadth of less than 10 $\mu$m.

* * * * *